United States Patent [19]

Hirama et al.

[11] Patent Number: 4,713,397
[45] Date of Patent: Dec. 15, 1987

[54] COMPOSITION FOR REDUCING NATURAL HAIR FALL-OUT

[75] Inventors: Shinichi Hirama, Kanagawa; Toshio Nishiyama, Tokyo; Youichi Ohta; Makoto Uzuka, both of Kanagawa; Kenichi Tomita, Tokyo; Keisuke Nakajima, Kanagawa; Kazumaro Furuse, Tokyo, all of Japan

[73] Assignee: Eisai Co., Ltd., Tokyo, Japan

[21] Appl. No.: 768,931

[22] Filed: Aug. 26, 1985

Related U.S. Application Data

[63] Continuation of Ser. No. 513,276, Jul. 13, 1983, abandoned.

[30] Foreign Application Priority Data

Jul. 15, 1982 [JP] Japan ................... 57-123527

[51] Int. Cl.$^4$ ............................................. A61K 31/12
[52] U.S. Cl. ................................. 514/690; 514/880; 514/881
[58] Field of Search .............. 514/688, 689, 690, 880, 514/881

[56] References Cited

U.S. PATENT DOCUMENTS

| 3,113,073 | 12/1963 | Grim | 514/689 |
|---|---|---|---|
| 3,317,381 | 5/1967 | Umehara | 424/94 |
| 3,426,125 | 2/1969 | Shigeta et al. | 424/94 |
| 3,499,088 | 3/1970 | Shinkai et al. | 424/94 |
| 4,009,174 | 2/1977 | Cluzan et al. | 514/929 |
| 4,031,205 | 6/1977 | Konishi | 424/94 |
| 4,073,910 | 2/1978 | Kawashima et al. | 514/866 |

FOREIGN PATENT DOCUMENTS

| 0023349 | 2/1981 | European Pat. Off. |
| 47-47663 | 12/1972 | Japan |
| 54-129132 | 10/1979 | Japan |
| 8201153 | 4/1981 | PCT Int'l Appl. |
| 964444 | 7/1964 | United Kingdom |
| 2116426 | 9/1983 | United Kingdom |

OTHER PUBLICATIONS

*Merck Index*, 9th ed., Abstract 9496, p. 1263, (1976).
*Current Therapy*, 1981, pp. 659–662, (1981).
*Current Therapy*, 1984, pp. 599–603, (1984).

Primary Examiner—Stanley J. Friedman
Assistant Examiner—F. Krosnick
Attorney, Agent, or Firm—Wenderoth, Lind & Ponack

[57] ABSTRACT

A composition for reducing hair fall-out comprising a ubiquinone (coenzyme $Q_n$) represented by the general formula:

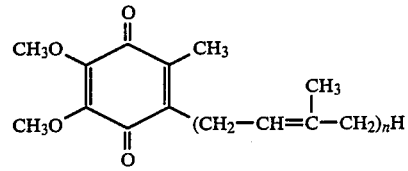

wherein n represents an integer of from 7 to 10. In addition to such a ubiquinone, the composition may contain a skin peripheral vasodilator drug, such as carpronium chloride, vitamin E nicotinate and benzyl nicotinate.

4 Claims, No Drawings

COMPOSITION FOR REDUCING NATURAL HAIR FALL-OUT

This application is a continuation of now abandoned application Ser. No. 513,276, filed July 13, 1983.

BACKGROUND OF THE INVENTION

1. Field of the Invention

The present invention relates to a composition for reducing hair fall-out, which comprises a ubiquinone, or a ubiquinone and a skin peripheral vasodilator drug.

2. Description of the Prior Art

Ubiquinones have been discovered from the mitochondria lipid of the heart of bovines by F. L. Crane in 1957. Presently, some ubiquinones are known, and they differ from each other only in the number (n) of isoprenoid side chains. Their action in vivo is not well known, but it is considered that they take part in an electron transport system to play a very important role in supplying energy required for cell activity.

SUMMARY OF THE INVENTION

The inventors have discovered that ubiquinone-containing drugs exhibit an effect of reducing hair fall-out, and also that although even a ubiquinone alone has this effect, ubiquinone combined with a skin peripheral vasodilator drug such as carpronium chloride, vitamin E nicotinate, or benzyl nicotinate exhibits an even more excellent effect.

It is therefore an object of the present invention to provide a composition for reducing hair fall-out, which comprises either a ubiquinone (coenzyme $Q_n$) represented by the general formula:

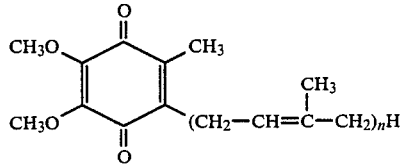

wherein n represents an integer of from 7 to 10, or such a ubiquinone and a skin peripheral vasodilator drug.

DETAILED DESCRIPTION OF THE INVENTION

Ubiquinones used in the present invention are those having 7 to 10 isoprenoid side chains, and among them, ubiquinone having 10 isoprenoid side chains (which will be referred to as ubiquinone-10 hereinafter) is particularly excellent. Ubiquinones may be incorporated in the composition, preferably in an amount within a range of 0.01 to 2% by weight.

Skin peripheral vasodilator drugs used in this invention are carpronium chloride, vitamin E nicotinates, or benzyl nicotinates, and one or more of them can be optionally selected. They may be preferably incorporated in the composition in an amount within a range of 0.1 to 2% by weight.

The composition according to the present invention has an excellent effect of reducing hair fall-out, and is also safe to use.

The present invention will now be more particularly described by the following tests and examples, but it should be noted that they are not intended in any way to limit the scope of the invention. All amounts are by weight.

TEST

The following test was carried out for the purpose of demonstrating the excellent hair fall-out reducing effect of the composition according to the present invention.

(1) Three samples as given below were used.

| (a) | Composition | % by weight |
|---|---|---|
| | 95% ethanol | 50 |
| | Ubiquinone-10 | 0.5 |
| | Panthotenyl ethyl ether | 0.1 |
| | Hardened castor oil-40 mole ethylene oxide adduct | 2 |
| | Ion-exchanged water | 47.4 |

A perfume and a coloring agent were incorporated in an appropriate amount.

| (b) | Composition | % by weight |
|---|---|---|
| | 95% ethanol | 50 |
| | Carpronium chloride | 1 |
| | Panthotenyl ethyl ether | 0.1 |
| | Hardened castor oil-40 mole ethylene oxide adduct | 2 |
| | Ion-exchanged water | 46.9 |

A perfume and a coloring agent were incorporated in an appropriate amount.

| (c) | Composition | % by weight |
|---|---|---|
| | 95% ethanol | 50 |
| | Ubiquinone-10 | 0.5 |
| | Carpronium chloride | 1 |
| | Panthotenyl ethyl ether | 0.1 |
| | Hardened castor oil-40 mole ethylene oxide adduct | 2 |
| | Ion-exchanged water | 46.4 |

A perfume and a coloring agent were incorporated in an appropriate amount.

(2) In this test, the effect was evaluated in terms of variation of the number of hairs falling out during washing of the hair before and after the test compositions were used. Panels to be subjected to the test were ten in number for each of the above-mentioned samples. Hairs fallen out were collected once a week: 16 times in total for a period of four months. This period of four months was divided into the following two periods: a period of an initial two months for collecting hairs naturally fallen out, and a period of the latter two months for collecting hair fallen out after application of the above samples to examine the effects upon the application thereof. Each effect was evaluated by comparing the average number of hairs fallen out which were collected eight times for a period before use of the test compositions (which will be referred to as the non-applied period hereinafter) with that of hairs fallen out which were similarly collected eight times for a period after application of the test compositions (which will be referred to as the applied period). The hairs were washed at intervals of every two days.

(3) Effect

As shown in Table I, with the sample (a), in which ubiquinone-10 is incorporated, the following data were obtained: among ten panels, a remarkably good effect (++) was shown in one panel; a good effect (+) in five panels; a slightly good effect (±) in two panels; and no effect (−) in two panels. This means that ubiquinone-10 has an excellent hair fall-out reducing effect.

As shown in Table II, with the sample (b), in which carpronium chloride is incorporated but ubiquinone is not incorporated, such good effects were not found, i.e., the following result was obtained: a remarkably good effect (++) was shown in none of the panels; a good effect (+) in two panels; a slightly good effect (±) in four panels; and no effect (−) in four panels.

As shown in Table III, with the sample (c), in which ubiquinone-10 and carpronium chloride are incorported, the following result was obtained: among ten panels, a remarkably good effect (++) was shown in five panels; a good effect (+) in three panels; a slightly good effect (±) in two panels. This means that while no effect is shown with skin peripheral vasodilator drugs, the addition of ubiquinone-10 thereto increases synergically the effect of ubiquinone-10. The criteria used in evaluation of the effects in the Tables are as follows:

| Reduction in numbers of hairs fallen out | |
| --- | --- |
| more than 70 | remarkably good effect (++) |
| more than 30 and less than 70 | good effect (+) |
| more than 10 and less than 30 | slightly good effect (±) |
| less than 10 | no effect (−) |

EXAMPLE 1

| Composition (of a lotion type) | % by weight |
| --- | --- |
| 95% ethanol | 85 |
| Ubiquinone-10 | 0.01 |
| Biotin | 0.01 |
| Hinokitiol | 0.01 |
| l-menthol | 0.2 |
| Ion-exchanged water | 14.77 |

In addition, a perfume and a coloring agent are incorported in an appropriate amount.

Preparation

Ubiquinone-10, biotin, hinokitiol, l-menthol, a perfume and a coloring agent are added to ethanol and dissolved therein by stirring, followed by adding ion-exchanged water to mix them, thereby to provide a clear liquid composition.

EXAMPLE 2

| Composition (of a lotion type) | % by weight |
| --- | --- |
| 95% ethanol | 50 |
| Ubiquinone-10 | 0.7 |
| Ubiquinone-7 | 0.3 |
| Carpronium chloride | 0.5 |
| Panthotenyl ethyl ether | 0.1 |
| Hardened castor oil-40 mole ethylene oxide adduct | 20 |
| Ion-exchanged water | 46.4 |

In addition, a perfume and a coloring agent are incorporated in an appropriate amount, respectively.

Preparation

The procedure was repeated as in Example 1.

EXAMPLE 3

| | Composition (of a cream type) | % by weight |
| --- | --- | --- |
| A: | Liquid paraffin | 38 |
| | Stearic acid | 2 |
| | White vaseline | 10 |
| | Ubiquinone-10 | 1 |
| | Vitamin E nicotinate | 0.1 |
| | Polyoxyethylene sorbitan mono-stearate | 3.8 |
| | Sorbitan mono-stearate | 4.2 |
| | Ethyl paraben | trace |
| B: | Triethanolamine | 1 |
| | Polyethylene glycol 1500 | 2 |
| | Ion-exchanged water | 37.9 |
| | Perfume | appropriate amount |

Preparation

The above oil phase (A) and aqueous phase (B) were heated to a temperature of 80° C., respectively, and mixed together for emulsification at the same temperature, followed by cooling the emulsified mass to ambient temperature with stirring, thereby to provide the composition.

EXAMPLE 4

| | Composition (of a milky lotion type) | % by weight |
| --- | --- | --- |
| A: | Purified jojoba oil | 10 |
| | Ubiquinone-10 | 2 |
| | Panthotenyl ethyl ether | 0.01 |
| | Benzyl nicotinate | 2 |
| | Lanolin | 2 |
| | Iso-propyl myristate | 2.5 |
| | Polyoxyethylene cetyl alcohol | 1.8 |
| | Sorbitan mono-stearate | 0.8 |
| | Ethyl paraben | trace |
| B: | Triethanolamine | 1 |
| | Glycerine | 4 |
| | Ion-exchanged water | 73.89 |
| | Perfume | appropriate amount |

Preparation

The above oil phase (A) and aqueous phase (B) were heated to a temperature of 80° C., respectively, and mixed together for emulsification at the same temperature, followed by cooling the emulsified mass to ambient temperature with stirring, thereby to provide the composition.

TABLE I

| Panel No. | Non-applied period | Applied period | Effect |
| --- | --- | --- | --- |
| 1 | 226 ± 51 | 203 ± 37 | ± |
| 2 | 193 ± 33 | 150 ± 29 | + |
| 3 | 343 ± 34 | 291 ± 61 | + |
| 4 | 234 ± 28 | 196 ± 31 | + |
| 5 | 156 ± 29 | 171 ± 41 | − |
| 6 | 369 ± 81 | 281 ± 74 | ++ |
| 7 | 403 ± 61 | 351 ± 45 | + |
| 8 | 311 ± 75 | 289 ± 61 | ± |
| 9 | 231 ± 29 | 179 ± 44 | + |
| 10 | 199 ± 61 | 196 ± 49 | − |

TABLE II

| Panel No. | Non-applied period | Applied period | Effect |
|---|---|---|---|
| 11 | 231 ± 61 | 232 ± 48 | − |
| 12 | 310 ± 89 | 303 ± 71 | − |
| 13 | 249 ± 54 | 226 ± 63 | ± |
| 14 | 199 ± 29 | 151 ± 28 | + |
| 15 | 333 ± 70 | 339 ± 61 | − |
| 16 | 401 ± 51 | 363 ± 49 | + |
| 17 | 267 ± 29 | 239 ± 51 | ± |
| 18 | 181 ± 38 | 163 ± 29 | ± |
| 19 | 280 ± 49 | 282 ± 61 | − |
| 20 | 232 ± 63 | 210 ± 56 | ± |

TABLE III

| Panel No. | Non-applied period | Applied period | Effect |
|---|---|---|---|
| 21 | 345 ± 81 | 260 ± 72 | ++ |
| 22 | 299 ± 71 | 212 ± 39 | ++ |
| 23 | 197 ± 29 | 151 ± 37 | + |
| 24 | 331 ± 61 | 283 ± 32 | + |
| 25 | 431 ± 101 | 403 ± 111 | ± |
| 26 | 312 ± 81 | 230 ± 62 | ++ |
| 27 | 228 ± 51 | 153 ± 42 | ++ |
| 28 | 233 ± 39 | 191 ± 27 | + |
| 29 | 342 ± 60 | 258 ± 44 | ++ |
| 30 | 293 ± 51 | 261 ± 70 | ± |

What we claim is:

1. A method of reducing natural fall-out of hair on a human, which comprises topically applying to the human an effective amount of a ubiquinone of the formula:

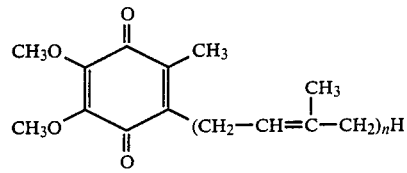

wherein n represents an integer of from 7 to 10.

2. A method according to claim 1, wherein the ubiquinone is ubiquinone-10.

3. A method according to claim 1, wherein the ubiquinone is applied as a composition which contains the ubiquinone and a skin peripheral vasodilator drug in a proportion of the ubiquinone to the skin peripheral vasodilator drug of 0.01–2:0.1–2 by weight.

4. A method according to claim 3, wherein the skin peripheral vasodilator drug is selected from the group consisting of carpronium chloride, vitamin E nicotinate and benzyl nicotinate.

* * * * *